(12) United States Patent
Pareek

(10) Patent No.: US 8,415,360 B2
(45) Date of Patent: Apr. 9, 2013

(54) PHARMACEUTICAL COMPOSITIONS FOR THE TREATMENT OF DIABETES MELLITUS

(75) Inventor: Anil Pareek, Mumbai (IN)

(73) Assignee: IPCA Laboratories Limited, Mumbai (IN)

( * ) Notice: Subject to any disclaimer, the term of this patent is extended or adjusted under 35 U.S.C. 154(b) by 0 days.

(21) Appl. No.: 13/119,648

(22) PCT Filed: Sep. 23, 2009

(86) PCT No.: PCT/IN2009/000521
§ 371 (c)(1),
(2), (4) Date: May 12, 2011

(87) PCT Pub. No.: WO2010/046910
PCT Pub. Date: Apr. 29, 2010

(65) Prior Publication Data
US 2011/0230501 A1    Sep. 22, 2011

(30) Foreign Application Priority Data
Sep. 24, 2008  (IN) .................... 2047/MUM/2008

(51) Int. Cl.
*A61K 31/4965*  (2006.01)
(52) U.S. Cl. .................. 514/255.06; 514/313
(58) Field of Classification Search ............. 514/255.06, 514/313
See application file for complete search history.

(56) References Cited

U.S. PATENT DOCUMENTS
3,174,901 A  *  3/1965  Sterne .......................... 514/635

FOREIGN PATENT DOCUMENTS
WO       0132758 A1      5/2001
WO    2007059372 A2      5/2007
WO   WO2007059372    *   5/2007

OTHER PUBLICATIONS

Gerstein et al., Diabetes Research and Clinical Practice, 55(3):209-219, 2002.*

Quatraro, et al., "Hydroxychloroquine in Decompensated, Treatment-Refractory Noninsulin-Dependent Diabetes Mellitus," Annals of Internal Medicine,1990, pp. 678-681, vol. 112, American College of Physicians, Philadelphia, PA, USA.

Gerstein, et al., "The Effectiveness of Hydroxychloroquine in Patients with Type 2 Diabetes Mellitus Who are Refractory to Sulfonylureas—a Randomized Trial," Diabetes Research and Clinical Practice, 2002, pp. 209-219, vol. 55, Elsevier, Maryland Heights, MO, USA.

Wasko, et al., "Hydroxychloroquine and Risk of Diabetes in Patients with Rheumatoid Arthritis," JAMA, 2007, pp. 187-193, vol. 298, No. 2, Chicago, IL, USA.

* cited by examiner

*Primary Examiner* — Rei-tsang Shiao
(74) *Attorney, Agent, or Firm* — Blank Rome LLP

(57) ABSTRACT

Disclosed herein is a pharmaceutical composition comprising Hydroxychloroquine or its pharmaceutically acceptable salt and at least one antidiabetic compound, useful in the treatment of diabetes mellitus.

19 Claims, No Drawings

PHARMACEUTICAL COMPOSITIONS FOR THE TREATMENT OF DIABETES MELLITUS

TECHNICAL FIELD OF INVENTION

The present invention relates to pharmaceutical compositions comprising combination of hydroxychloroquine with antidiabetic drug(s). More particularly, the invention relates to synergistic combinations of hydroxychloroquine and at least one antidiabetic drug selected from sulphonylureas, biguanides and thiazolidinediones. The present invention also relates to the use of synergistic compositions according to the invention for the treatment of diabetes mellitus and methods of treatment of diabetes mellitus thereof.

BACKGROUND OF THE INVENTION

Diabetes mellitus is a common disorder associated with high morbidity and mortality. Though, it is more prevalent in developed countries, its incidence in developing countries is steadily increasing due to rapid changes in lifestyle. Type 2 diabetes affects up to 10% of all adults in the general population and up to 20% of people aged over 65, and is a major risk factor for cardiovascular, eye, kidney, and nerve disease. (*National Institutes of Health, NIH Publication No.* 95-1468, 1995, pp. 47-68.)

Several antidiabetic agents with different mechanisms of action are known for use in the treatment of diabetes Mellitus. Sulphonylureas and biguanides have been mainstay of therapy in diabetes mellitus. Though oral monotherapy is successful in initial stages of treatment, however, it is often associated with a high secondary failure rate on continued use, which contributes to the development of long term diabetes complications as a result of persistent hyperglycemia. (*Am J. Med.* 2000 Apr. 17; 108 Suppl 6a:15S-22S.)

In order to reduce and maintain blood glucose levels in normal ranges, evidences suggest that combination therapy using oral antidiabetic agents with different mechanisms of action may be effective. Such combination therapy offers not only enhanced glycaemic control, but also reduces adverse reactions and thus better outcomes in the management of diabetes.

One such combination known is that of sulphonylurea compounds plus metformin, which is somewhat effective in solving the underlying defects in the disorder, i.e., both insulin deficiency and insulin resistance. Sulphonylurea compounds commonly used in medicinal application includes Glimipiride, Glipizide, Gliclazide, and Glibenclamide.

Sulphonylurea derivatives act by binding to sulphonylurea receptors on pancreatic β-cells, leading to increased secretion of insulin. Possible mechanism of actions of metformin includes inhibition of hepatic gluconeogenesis by decreasing hepatic insulin resistance; delaying/inhibiting absorption of glucose from the gastrointestinal tract and increasing the insulin sensitivity and glucose uptake in the cells.

Often patients on combination therapy with sulphonylureas and metformin are not controlled and hence the option left is either addition of third drug or put patient on insulin therapy. Insulin therapy is not only costly but is not preferred due to poor patient compliance in parenteral application. New generation thiazolidinediones class of antidiabetic drugs, though useful in glycemic control, are associated with several adverse effects such as excessive risk of congestive heart failure, acute myocardial infarction, increased rate of bone loss and liver toxicity.

In the light of failure of monotherapy of antidiabetic drugs in glycemic control and increased adverse effects when administered at high doses of antidiabetic drugs for getting better glycemic control, newer medications for diabetes are needed, which will have good antihyperglycemic effect, as well as good tolerability profile.

Since Diabetes is also associated with risk of Coronary Heart disease (CHD) or increase in CHD incidence, a drug reducing blood glucose levels while giving cardiovascular benefits is preferable for the treatment of diabetes.

Hydroxychloroquine is a disease modifying antirheumatic drug (DMARD) and is being used in rheumatology for past four decades. The use of hydroxychloroquine is well established in rheumatoid arthritis and systemic lupus erythematosus.

Hydroxychloroquine is reported to show antidiabetic properties in many studies. However, the mechanism by which hydroxychloroquine improves glucose control remains unclear (*Diabetes Res Clin Pract.* 2002 March; 55(3):209-19).

The glucose lowering efficacy of hydroxychloroquine has been studied in various clinical trials. A study conducted in 135 obese patients with diabetes mellitus, showed that hydroxychloroquine improved glycemic control in sulphonylurea-refractory patients with poorly controlled Type 2 diabetes. (*Diabetes Res Clin Pract.* 2002 March; 55(3):209-19.) In another multicenter observational study of 4905 adults with rheumatoid arthritis indicated that use of hydroxychloroquine is associated with a reduced risk of diabetes. (*JAMA.* 2007 Jul. 11; 298(2):187-93). The reduction in blood glucose level is not very significant for making hydroxychloroquine as a monotherapy. It is being suggested as a prophylactic measure to prevent development of diabetes in patients with rheumatoid arthritis.

Hydroxychloroquine has shown efficacy in patients with resistant diabetes also. A study conducted in 38 patients with non insulin-dependent diabetes resistant to commonly used therapies (oral drugs, insulin, combination of insulin and oral drugs) showed statistically significant improvement in patients who received the insulin and Hydroxychloroquine which was compared with combination of glibenclamide with hydroxychloroquine. It was possible to reduce the daily insulin dose in patients treated with the combined insulin and hydroxychloroquine therapy by an average of 30%. The trial reveals that combining antidiabetic therapy with hydroxychloroquine in decompensated, treatment-refractory patients with noninsulin-dependent diabetes may help to break the vicious circle of hyperglycemia and lead to better management of the disease. (*Ann Intern Med.* 1990 May 1; 112(9): 678-81)

Along with antihyperglycaemic effects, hydroxychloroquine is also associated with cardiovascular benefits, due to its lipid lowering effect and antiplatelet effect.

Improvement of serum cholesterol in patients treated with hydroxychloroquine has been reported. These include a decrease in serum levels of cholesterol by approximately 10% and an increase in low-density lipoprotein receptors. Hydroxychloroquine also led to a rise in both HDL and % HDL. (*Ann Rheum Dis.* 1997 June; 56(6):374-7.)

Hydroxychloroquine therapy had a high statistical association with low serum levels of cholesterol, triglycerides, and LDL, irrespective of concomitant steroid administration. The hydroxychloroquine-treated group had lower cholesterol and LDL levels than those receiving neither hydroxychloroquine nor steroids. Very-low-density lipoprotein cholesterol was reduced in the group receiving hydroxychloroquine, and this was associated with decreased plasma triglycerides in this group. (*Br J Rheumatol.* 1985 August; 24(3):250-5.)

In addition to its lipid lowering effect, hydroxychloroquine may be cardioprotective by reducing platelet aggregation.

Hydroxychloroquine causes reduction in red blood cell aggregation without prolonging the bleeding time in humans and experimentally, reduces the size of the thrombus. There is a variably demonstrable reduction in platelet aggregation and blood viscosity in humans. (*Am J Med.* 1988 Oct. 14; 85(4A): 57-61)

A more recent clinical study found a significant reduction in plasma viscosity as well as whole blood viscosity in post-operative patients treated with hydroxychloroquine.

WO/2001/032758 discloses Pharmaceutical composition comprising a combination of metformin with other anti diabetic drug, wherein the other antidiabetic agent is one or more of glyburide, glimepiride, glipyride, glipizide, chlorpropamide, gliclazide, acarbose, miglitol, troglitazone, rosiglitazone, pioditazone, insulin and/or KRP-297.

In the light of failure of monotherapy of antidiabetic drugs in getting good glycemic control and increased adverse effects when administered at higher doses of antidiabetic drugs for getting better glycemic control, it is an object of the present invention to seek newer medication for the treatment of diabetes mellitus, a chronic disease. Surprisingly, combination of hydroxychloroquine with antidiabetic drugs such as sulphonylureas, biguanides and thiazolidinediones found to be an effective treatment for diabetes mellitus, meeting the object of the present invention.

SUMMARY OF THE INVENTION

Accordingly, in one aspect, the present invention provides a pharmaceutical composition comprising a combination of hydroxychloroquine and at least one antidiabetic drug(s). In a preferred embodiment, the present invention provides synergistic compositions of hydroxychloroquine or its salt combined with at least one anti-diabetic compound selected from the class of sulphonylureas, biguanides and thiazolidinediones compounds.

In another aspect, the present invention provides a method of treatment of diabetes comprising administering a pharmaceutically effective amount of hydroxychloroquine or its pharmaceutically acceptable salt in conjunction with a non-insulin antidiabetic agent. In an embodiment, the antidiabetic agent is selected from sulphonylureas, biguanides and thiazolidinediones class of compounds, preferably in a fixed pharmaceutical composition containing hydroxychloroquine. In another embodiment, the invention provides a method of treatment of diabetes which is resistant to oral hyperglycemic agents. In a preferred embodiment, the invention provides a method of treatment of diabetes associated with risk of hyperlipidemia or platelet aggregation. Use of synergistic compositions of the present invention for the treatment of diabetes, particularly diabetes associated with hyperlipidemia is within the metes and bounds of the invention.

DETAILED DESCRIPTION OF THE INVENTION

The invention will now be described in detail in connection with certain preferred and optional embodiments, so that various aspects thereof may be more fully understood and appreciated.

The present invention provides a pharmaceutical composition comprising a combination of hydroxychloroquine and non-insulin antidiabetic drugs. Preferably the composition of the present invention comprises a fixed dose of hydroxychloroquine and at least one antidiabetic drug selected from the group of sulphonylurea, biguanide and thiazolidinedione compounds. In the composition hydroxychloroquine or the antidiabetic compound may be present in free form or in any of its pharmaceutically acceptable salt form and may be present as physically separable or physically inseparable state/form. Preferred salts of hydroxychloroquine are sulphate and phosphate salts.

The sulfonylurea class of antidiabetic compounds may be preferably selected from Glimepiride, Glipizide, Glibenclamide, Gliclazide or the like, whereas, metformin is preferred in biguanide class of antidiabtetic compounds. Among thiazolidinediones class of antidiabteic compounds, Pioglitazone and Rosiglitazone are preferred.

Accordingly, the combination of the present invention comprises therapeutically effective amount of hydroxychloroquine and at least one antidiabetic compound selected from sulphonylureas, biguanides and thiazolidinediones for treatment of diabetes mellitus, preferably in a fixed dose combination.

The term "therapeutically effective amount" means the amount which provides the desired therapeutic effect on administration of the same.

Therapeutic effective amount can be determined by a skilled artisan according to bodyweight of patient, route of administration and condition of disease in a conventional manner. Hydroxychloroquine dose may be generally be administered in the range of 50 mg to 400 mg, when it is administered in conjunction with other anti diabetics such as sulphonylureas, biguanides and thiazolidinediones, though it can vary depending upon patient condition and the glycemic control needed.

According to a preferred embodiment, the invention discloses a fixed dose pharmaceutical composition which comprises hydroxychloroquine in combination with sulfonylureas antidiabetic compounds. Dosing for individual sulfonyl urea may be adjusted based on the therapeutic range of each compound, for example, Glimepiride can be used in the range of 1 mg to 20 mg in the fixed dosage form in combination with hydroxychloroquine for an average adult.

Similarly, the fixed dose composition of the present invention comprises hydroxychloroquine and gliclazide. The normal dose of gliclazide ranges from an amount of 30 mg to 320 mg. Further, the present invention describes fixed dose pharmaceutical composition that comprises hydroxychloroquine with glibenclamide in which Glibenclamide quantity may be present in the ranges of 1 mg to 20 mg. The present invention further discloses a pharmaceutical composition which comprises hydroxychloroquine in combination with Glipizide, wherein Glipizide dose may be selected from an amount of 1 mg to 40 mg in the composition.

According to another preferred embodiment, the invention discloses a fixed dose pharmaceutical composition which comprises hydroxychloroquine in combination with biguanides, preferably Metformin. The fixed dose composition of hydroxychloroquine and metformin comprises, for example, but not limited to, hydroxychloroquine in amount of 50 mg to 400 mg and metformin in an amount of 200 mg to 2500 mg.

According to another preferred embodiment, the invention discloses a fixed dose pharmaceutical composition which comprises hydroxychloroquine in combination with thiazolidinedione compounds, preferably Rosiglitazone or Pioglitazone. The fixed dose composition comprises hydroxychloroquine in amount of, for example, but not limited, 50 mg to 400 mg and Rosiglitazone in an amount of 1 mg to 8 mg, or pioglitazone in amount of 10 mg to 45 mg, respectively.

The quantity of the compound/compounds used in fixed dose pharmaceutical compositions of the present invention will vary depending upon the body weight of the patient and the mode of administration and can be of any effective amount to achieve the desired therapeutic effect.

In another aspect, the present invention provides a method of treatment of diabetes comprising administering a pharmaceutically effective dose of a hydroxychloroquine or its pharmaceutically acceptable salt in conjunction with a non-insulin antidiabetic agent, preferably in a fixed dose composition according to the invention. The diabetes is especially resistant to insulin or other antihyperglycemic drugs, and may be associated with risk of hyperlipidemia and/or platelet aggregation.

The method of treatment according to the invention is especially advantageous in patients with diabetes, especially complicated or resistant diabetes. Present method of treatment improves glucose lowering efficacy in a synergistic manner, thus effecting significant improvement in glycaemic control in drug resistant diabetes mellitus. The present treatment not only reduces dosage of oral hypoglycaemic agents for giving better glycemic control but also provides cardiovascular benefits by reducing platelet aggregation and lipid levels, improving total protein and albumin levels and reducing urea level.

Therefore, the fixed dose combination of hydroxychloroquine with antidiabetic drugs such as sulphonylureas, biguanides and thiazolidinediones, according to the present invention, will provide a useful treatment option for patients with diabetes mellitus.

The combination of Hydroxychloroquine with antidiabetic drugs according to the present invention will offer following advantages:
1. Synergistic effect on glucose lowering capacity in diabetes treatment.
2. Significant improvement in glycaemic control in patients with diabetes resistant to oral hypoglycaemic agents (such as sulphonylureas, biguanides and thiazolidinediones), insulin or combination of insulin and oral drugs
3. Reduces dose levels of oral hypoglycaemic agents as well as insulin, while giving better glycaemic control.
4. Cardiovascular benefits from reducing the lipid levels,
5. Reduction of platelet aggregation and blood viscosity
6. Low toxicity profile compared to monotherapy requiring higher doses of hypoglycemic agents.

The fixed dose composition of the present invention can be prepared in any conventional dosage form. The fixed dose formulation of the present invention is preferably in the form of tablets or capsules, wherein tablets/capsules can be prepared in immediate release, modified/controlled release, extended or in sustain release form. Dosage form may be, for example, but not limited to, a multilayer tablet, a two-layer tablet, or capsules or sachets containing the active ingredients in separate granulates or beads, either granulate or bead, optionally being coated with a protective coating or an enteric-coating. The present invention encompasses oral solutions, suspensions and parenteral administration.

The fixed dose composition of hydroxychloroquine with other antidiabetic drugs such as sulphonylureas, biguanides and thiazolidinediones can be prepared in suitable dosage form by combining with at least one pharmaceutical carrier/excipient according to known formulation techniques.

As used herein the term 'at least one pharmaceutical carrier/excipient' refers to any conventional pharmaceutical carrier/excipient routinely used in preparation of desired dosage forms like solid; liquid and injectable dosage forms. For oral use, suitable pharmaceutical carriers include inert diluents or fillers thereby forming oral dosage forms such as tablets, powders, pellets, capsules, syrups or suspensions and the like.

For example, tablets may contain variety of excipients such as disintegrants, for example, starch, complex silicates together with binding agents such as poly vinyl pyrrolidone, sucrose, gelatin and acacia; lubricants, for example, magnesium silicate, sodium lauryl sulfate and talc etc. often used in tabletting processes. Solid compositions of the present invention can also be filled into soft and hard gelatin capsules.

For soft gelatin capsule, the composition may be solubilized in suitable vegetable or edible oil such as sunflower oil, corn oil, peanut oil or any other suitable oil.

The pharmacological effects of combination therapy compared to monotherapy was established by conducting comparative, open label pre-clinical (animal) study and evaluating the efficacy in terms of potency of present composition of combination of hydroxychloroquine and antidiabetic drugs such as sulphonylureas, biguanides and thiazolidinediones in reducing blood glucose level, reducing LDL cholesterol, lowering Triglycerides, and effects on HDL and body weight gain.

The results of safety, efficacy and synergy of the fixed dose combinations of hydroxychloroquine with other antidiabetic drugs selected drugs such as sulphonylureas, biguanides and thiazolidinediones is clinically established by the following experiments.

The following examples, which include preferred embodiments, will serve to illustrate the practice of this invention, it being understood that the particulars shown are by way of example and for purpose of illustrative discussion of preferred embodiments of the invention.

Pharmacological Evaluation of Combination of Hydroxychloroquine with Glimepiride Thirty Wistar rats weighing 150-200 g of either sex were divided into six groups consisting of five rats each. Experimental diabetes was induced in rats by injecting alloxan monohydrate intraperitonially at a dose of 90 mg/kg body weight. Rats with blood sugar level of 250-350 mg/dl, were considered as diabetic and employed in the study.

Group 1 (normal control) consisted of normal rats that neither received alloxan monohydrate nor any drug. Group 2' served as diabetic control which received vehicle orally. Group 3 was diabetic and treated with hydroxychloroquine (HCQ) at the dose of 160 mg/kg; p.o. Group 4 was diabetic and treated with glimepiride (GLM) at the dose of 8 mg/kg; p.o. Group 5 was diabetic and treated with low dose combination of GLM (4 mg/kg) and HCQ (80 mg/kg), whereas Group 6 was diabetic and treated with high dose combination of GLM (8 mg/kg) and HCQ (160 mg/kg). The study drugs were administered for nine days.

There was a significant difference between the treated groups with respect to fall in blood glucose levels. Both (low dose and high dose) combination treatment showed significantly more fall in blood glucose levels as compared to individual treatment groups ($p<0.05$; $p<0.001$ for low dose and high dose respectively). Moreover the fall in blood glucose of high dose combination group was significantly more than low dose combination treated group ($p=0.001$). Reduction in body weight was significantly lower in case of animals treated with high dose combination of HCQ and GLM than in animals treated with their individual components and in group treated with low dose combination. Moreover, both the high and low dose combination significantly ($p<0.05$) reduced the total cholesterol, triglyceride levels and increased the HDL, hemoglobin, protein and albumin levels significantly ($p<0.05$) compared to diabetic control group. Results of study is summarized in table 1:

TABLE 1

| Group | Dose (mg/kg/day) | Blood Glucose (mg/dl) (% mean change) | | Body Weight (g) (% mean change) | | Biochemical Parameters | |
|---|---|---|---|---|---|---|---|
| | | Initial | Final | Initial | Final | TG (mg/dl) | TC (mg/dl) |
| Normal | — | 97.00 ± 4.0 | 96.40 ± 2.88 (−0.56)$^a$ | 173.6 ± 12.46 | 184.20 ± 13.17 (6.11)$^a$ | 98.60 ± 4.56$^c$ | 118.60 ± 4.67$^d$ |
| Diabetic | — | 280 ± 21.21 | 286.20 ± 20.92 (2.23)$^b$ | 172.40 ± 9.20 | 147.20 ± 8.22 (−14.54)$^b$ | 134.4 ± 9.32$^a$ | 193.60 ± 6.27*$^a$ |
| HCQ | 160 | 296.00 ± 15.93 | 263.80 ± 2.04 (−10.81)$^c$ | 169.2 ± 10.20 | 151.60 ± 13.16 (−10.51)$^b$ | 117.20 ± 2.28$^b$ | 178.40 ± 2.70$^c$ |
| GLM | 8 | 295.2 ± 23.08 | 157.2 ± 17.64 (−46.83)$^d$ | 176 ± 11.46 | 170 ± 11.22 (−3.40)$^c$ | 113.40 ± 3.64$^b$ | 169.40 ± 7.05$^b$ |
| HCQ + GLM | 80 + 4 | 300 ± 12.24 | 147 ± 6.55 (−50.97)$^e$ | 169.4 ± 13.39 | 163 ± 14.23 (−3.82)$^c$ | 115.20 ± 8.34$^b$ | 178.80 ± 5.89$^b$ |
| HCQ + GLM | 160 + 4 | 323.4 ± 15.48 | 131.4 ± 10.47 (−59.37)$^f$ | 185.20 ± 12.25 | 176.2 ± 11.38 (−4.84)$^c$ | 118.2 ± 7.98$^b$ | 162.6 ± 12.85$^b$ |

| | Biochemical Parameters | | | | |
|---|---|---|---|---|---|
| Group | HDL (mg/dl) | Protein (T) (g/dl) | Alb. (g/dl) | Urea (mg/dl) | Hb (g/dl) |
| Normal | 37.40 ± 1.14$^c$ | 7.93 ± 0.77$^c$ | 5.59 ± 0.68$^c$ | 26.13 ± 2.47$^c$ | 16.16 ± 1.14$^c$ |
| Diabetic | 25.80 ± 1.92$^a$ | 4.47 ± 0.57$^a$ | 3.74 ± 0.47$^a$ | 40.08 ± 2.38$^a$ | 10.54 ± 1.34$^a$ |
| HCQ | 35.80 ± 2.28$^b$ | 6.06 ± 1.43$^b$ | 4.03 ± 0.13$^a$ | 29.70 ± 1.37$^b$ | 12.12 ± 1.27$^a$ |
| GLM | 33 ± 1.58$^b$ | 5.78 ± 1.22$^b$ | 3.99 ± 0.24$^a$ | 30.26 ± 0.86$^b$ | 14.04 ± 1.90$^b$ |
| HCQ + GLM | 35 ± 2.23$^b$ | 7.01 ± 0.41$^b$ | 4.096 ± 0.20$^a$ | 31.7 ± 1.81$^b$ | 13.28 ± 2.39$^b$ |
| HCQ + GLM | 33.80 ± 2.49$^b$ | 6.98 ± 1.60$^b$ | 4.52 ± 0.51$^b$ | 30.39 ± 1.32$^b$ | 15.88 ± 1.74$^b$ |

Values are expressed as Mean ± S.D. (n = 5).
Values in the same column with different superscript are significantly different ($p < 0.05$).
Hydroxychloroquine: HCQ;
Glimepiride: GLM;
Triglyceride: TG;
Total Cholesterol: TC;
High Density Lipoprotein: HDL;
Albumin: Alb;
Hemoglobin: Hb
Total Protein: Protein (T)

The results demonstrates that GLM and HCQ at a dose of 4 mg & 80 mg provides blood glucose reduction of −50.97 compared to 46.83% in 8 mg glimepiride monotherapy and −10.81% in 160 mg hydroxychloroquine monotherapy, respectively. Combination significantly ($p<0.05$) reduced the total cholesterol, triglyceride levels and increased the HDL, hemoglobin, protein and albumin levels significantly ($p<0.05$) compared to diabetic control group.

Pharmacological Evaluation of Combination of Hydroxychloroquine with Metformin

Thirty Wistar rats weighing 150-200 g of either sex were divided into six groups consisting of five rats each. Experimental diabetes was induced in rats by injecting alloxan monohydrate intraperitonially at a dose of 90 mg/kg body weight. Rats with blood sugar level of 250-350 mg/dl, were considered as diabetic and employed in the study. Group 1 (normal control) consisted of normal rats that neither received alloxan monohydrate nor any drug. Group 2 served as diabetic control which received vehicle orally. Group 3 was diabetic and treated with hydroxychloroquine (HCQ) at the dose of 160 mg/kg; p.o. Group 4 was diabetic and treated with metformin (MET) at the dose of 500 mg/kg; p.o. Group 5 was diabetic and treated with low dose combination of MET (250 mg/kg) and HCQ (80 mg/kg), whereas Group 6 was diabetic and treated with high dose combination of MET (500 mg/kg) and HCQ (160 mg/kg). The study drugs were administered for nine days.

There was a significant difference between the treated groups with respect to fall in blood glucose levels. Both (low dose and high dose) combination treatment showed significantly more fall in blood glucose levels as compared individual treatment groups. ($p=0.04$; $p=0.001$ for low dose and high dose respectively). Moreover the fall in blood glucose of high dose combination group was significantly more than low dose combination treated group ($p=0.015$). Reduction in body weight of animals treated with high and low dose combination of HCQ and MET was significantly lower ($P<0.05$) than the diabetic control group. Moreover, both the high and low dose combination significantly ($p<0.05$) reduced the total cholesterol, triglyceride levels and increased the HDL, hemoglobin, protein and albumin levels significantly ($p<0.05$) compared to diabetic control group.

Results of study is summarized in table 2.

TABLE 2

| Group | Dose (mg/kg/day) | Blood Glucose (mg/dl) (% mean change) Initial | Blood Glucose (mg/dl) (% mean change) Final | Body Weight (g) (% mean change) Initial | Body Weight (g) (% mean change) Final | Biochemical Parameters TG (mg/dl) | Biochemical Parameters TC (mg/dl) |
|---|---|---|---|---|---|---|---|
| Normal | — | 97.00 ± 4.0 | 96.40 ± 2.88 $(-0.56)^a$ | 173.6 ± 12.46 | 184.20 ± 13.17 $(6.11)^a$ | 98.60 ± 4.56$^c$ | 118.60 ± 4.67$^d$ |
| Diabetic | — | 280 ± 21.21 | 286.20 ± 20.92 $(2.23)^b$ | 172.40 ± 9.20 | 147.20 ± 8.22 $(-14.54)^b$ | 134.4 ± 9.32$^a$ | 193.60 ± 6.27$^a$ |
| HCQ | 160 | 296.00 ± 15.93 | 263.80 ± 2.04 $(-10.81)^c$ | 169.2 ± 10.20 | 151.60 ± 13.16 $(-10.51)^b$ | 117.20 ± 2.28$^b$ | 178.40 ± 2.70$^c$ |
| MET | 500 | 283.4 ± 23.49 | 148.8 ± 17.35 $(-47.58)^d$ | 181.2 ± 10.40 | 173.8 ± 7.19 $(-10.51)$ c | 111.20 ± 5.93$^b$ | 170.40 ± 5.90$^b$ |
| HCQ + MET | 80 + 250 | 284.4 ± 15.32 | 135.4 ± 8.67 $(-52.40)^e$ | 175.0 ± 11.55 | 168.20 ± 11.03 $(-3.87)$ c | 112.80 ± 3.03$^b$ | 164.40 ± 5.0$^b$ |
| HCQ + MET | 160 + 500 | 307.2 ± 17.02 | 136.80 ± 7.15 $(-55.44)^f$ | 175.80 ± 13.55 | 169.4 ± 14.77 $(-3.70)$ c | 117.60 ± 9.94$^b$ | 168.0 ± 13.60$^b$ |

| Group | Biochemical Parameters HDL (mg/dl) | Protein (T) (g/dl) | Alb. (g/dl) | Urea (mg/dl) | Hb (g/dl) |
|---|---|---|---|---|---|
| Normal | 37.40 ± 1.14$^c$ | 7.93 ± 0.77$^c$ | 5.59 ± 0.68$^c$ | 26.13 ± 2.47$^c$ | 16.16 ± 1.14$^c$ |
| Diabetic | 25.80 ± 1.92$^a$ | 4.47 ± 0.57$^a$ | 3.74 ± 0.47$^a$ | 40.08 ± 2.38$^a$ | 10.54 ± 1.34$^a$ |
| HCQ | 35.80 ± 2.28$^b$ | 6.06 ± 1.43$^b$ | 4.03 ± 0.13$^a$ | 29.70 ± 1.37$^b$ | 12.12 ± 1.27$^a$ |
| MET | 34.40 ± 2.51$^b$ | 6.75 ± 0.80$^b$ | 4.52 ± 1.12$^a$ | 31.49 ± 1.81$^b$ | 12.80 ± 1.25$^b$ |
| HCQ + MET | 34.80 ± 0.83$^b$ | 7.39 ± 0.48$^b$ | 4.09 ± 0.27$^a$ | 32.75 ± 2.44$^b$ | 13.32 ± 0.75$^b$ |
| HCQ + MET | 35.40 ± 2.51$^b$ | 8.14 ± 0.56$^b$ | 5.01 ± 0.25$^b$ | 29.92 ± 1.04$^b$ | 15.12 ± 2.01$^b$ |

Values are expressed as Mean ± S.D. (n = 5).
Values in the same column with different superscript are significantly different ($p < 0.05$).
Hydroxychloroquine: HCQ;
Metformin: MET;
Triglyceride: TG;
Total Cholesterol: TC;
High Density Lipoprotein: HDL;
Albumin: Alb;
Hemoglobin: Hb
Total Protein: Protein (T)

The present study demonstrates that metformin and HCQ at a dose of 250 mg & 80 mg provides blood glucose reduction of −52.40 compared to 47.58% in 500 mg Metformin monotherapy and −10.81% in 160 mg hydroxychloroquine monotherapy, respectively, indicating half the dose of monotherapy gives significantly higher glycemic control over monotherapy. Combination significantly ($p<0.05$) reduced the total cholesterol, triglyceride levels and increased the HDL, hemoglobin, protein and albumin levels significantly ($p<0.05$) compared to diabetic control group.

Pharmacological Evaluation of Combination of Hydroxychloroquine with Pioglitazone Thirty Wistar rats weighing 150-200 g of either sex were divided into six groups consisting of five rats each. Experimental diabetes was induced in rats by injecting alloxan monohydrate intraperitoneally at a dose of 90 mg/kg body weight. Rats with blood sugar level of 250-350 mg/dl, were considered as diabetic and employed in the study. Group 1 (normal control) consisted of normal rats that neither received alloxan monohydrate nor any drug. Group 2 served as diabetic control which received vehicle orally. Group 3 was diabetic and treated with Hydroxychloroquine (HCQ) at the dose of 160 mg/kg; p.o. Group 4 was diabetic and treated with pioglitazone (PIO) at the dose of 10 mg/kg; p.o. Group 5 was diabetic and treated with low dose combination of PIO (6 mg/kg) and HCQ (80 mg/kg), whereas Group 6 was diabetic and treated with high dose combination of PIO (10 mg/kg) and HCQ (160 mg/kg). The study drugs were administered for nine days.

Administration of high dose combination of HCQ and PIO resulted in significant ($P<0.001$) reduction in blood glucose levels as compared to their individual components in alloxan induced diabetic rats. However in case of low dose combination treated group the reduction in blood glucose level was not significantly different from their individual components. The fall in blood glucose of high dose combination group was significantly more than low dose combination treated group ($p<0.001$). Reduction in body weight of animals treated with high and low dose combination of HCQ and PIO was significantly lower ($P<0.05$) than the diabetic control group. Moreover, both the high and low dose combination significantly ($p<0.05$) reduced the total cholesterol, triglyceride levels and increased the HDL, hemoglobin, protein and albumin levels significantly ($p<0.05$) compared to diabetic control group.

Results of study is summarized in table 3

TABLE 3

| Group | Dose (mg/kg/day) | Blood Glucose (mg/dl) (% mean change) Initial | Blood Glucose (mg/dl) (% mean change) Final | Body Weight (g) (% mean change) Initial | Body Weight (g) (% mean change) Final | Biochemical Parameters TG (mg/dl) | Biochemical Parameters TC (mg/dl) |
|---|---|---|---|---|---|---|---|
| Normal | — | 97.00 ± 4.0 | 96.40 ± 2.88 (−0.56)$^a$ | 173.6 ± 12.46 | 184.20 ± 13.17 (6.11)$^a$ | 98.60 ± 4.56$^c$ | 118.60 ± 4.67$^d$ |
| Diabetic | — | 280 ± 12.21 | 286.20 ± 20.92 (2.23)$^b$ | 172.40 ± 9.20 | 147.20 ± 8.22 (−14.54)$^b$ | 134.4 ± 9.32$^a$ | 193.60 ± 6.27$^a$ |
| HCQ | 160 | 296.00 ± 15.93 | 263.80 ± 2.04 (−10.81)$^c$ | 169.2 ± 10.20 | 151.60 ± 13.16 (−10.51)$^b$ | 117.20 ± 2.28$^b$ | 178.40 ± 2.70$^c$ |
| PIO | 10 | 302.8 ± 12.21 | 175.8 ± 5.48 (−41.92)$^a$ | 169.4 ± 9.91 | 159.20 ± 11.21 (−6.07)$^a$ | 117.2 ± 2.28$^b$ | 178.4 ± 2.70$^b$ |
| HCQ + PIO | 80 + 6 | 289.2 ± 18.08 | 155.6 ± 8.32 (−46.16)$^a$ | 172.0 ± 9.97 | 162.00 ± 8.51 (−5.78)$^a$ | 113.2 ± 7.42$^b$ | 184.2 ± 6.97$^b$ |
| HCQ + PIO | 160 + 10 | 336 ± 7.34 | 142.40 ± 14.97 (−57.63)$^a$ | 168.2 ± 9.83 | 161.00 ± 10.31 (−4.3)$^a$ | 123.2 ± 10.94$^b$ | 159.2 ± 9.65$^b$ |

| Group | Biochemical Parameters HDL (mg/dl) | Protein (T) (g/dl) | Alb. (g/dl) | Urea (mg/dl) | Hb (g/dl) |
|---|---|---|---|---|---|
| Normal | 37.40 ± 1.14$^c$ | 7.93 ± 0.77$^c$ | 5.59 ± 0.68$^c$ | 26.13 ± 2.47$^c$ | 16.16 ± 1.14$^c$ |
| Diabetic | 25.80 ± 1.92$^a$ | 4.47 ± 0.57$^a$ | 3.74 ± 0.47$^a$ | 40.08 ± 2.38$^a$ | 10.54 ± 1.34$^a$ |
| HCQ | 35.80 ± 2.28$^b$ | 6.06 ± 1.43$^b$ | 4.03 ± 0.13$^b$ | 29.70 ± 1.37$^b$ | 12.12 ± 1.27$^a$ |
| PIO | 35.8 ± 2.28$^b$ | 6.06 ± 1.43$^b$ | 4.03 ± 0.14$^b$ | 29.69 ± 1.37$^b$ | 12.12 ± 1.27$^b$ |
| HCQ + PIO | 34.6 ± 2.70$^b$ | 5.69 ± 0.92$^b$ | 4.30 ± 0.35$^a$ | 31.80 ± 2.42$^b$ | 12.08 ± 1.38$^b$ |
| HCQ + PIO | 32.8 ± 3.89$^b$ | 7.07 ± 0.98$^b$ | 3.79 ± 0.38$^b$ | 31.08 ± 1.14$^b$ | 14.2 ± 1.55$^b$ |

Values are expressed as Mean ± S.D. (n = 5).
Values in the same column with different superscript are significantly different ($p < 0.05$).
Hydroxychloroquine: HCQ;
Metformin: MET;
Triglyceride: TG;
Total Cholesterol: TC;
High Density Lipoprotein: HDL;
Albumin: Alb;
Hemoglobin: Hb
Total Protein: Protein (T)

The results shows that Pioglitazone and HCQ at a dose of 6 mg & 80 mg provides blood glucose reduction of −46.16 compared to 41.92% with 10 mg Pioglitazone monotherapy and −10.81% with 160 mg hydroxychloroquine monotherapy, respectively, indicating almost half the dose of monotherapy gives significantly higher glycemic control. About 57.63% reduction in blood glucose observed in high dose combination [HCQ (160 mg)/pioglitazone (10 mg)] group compared to 41.92% in monotherapy at same dose of pioglitazone alone, which is clinically very significant. Combination significantly ($p<0.05$) reduced the total cholesterol, triglyceride levels and increased the HDL, hemoglobin, protein and albumin levels significantly ($p<0.05$) compared to diabetic control group.

EXAMPLES

Example 1

Fixed Dose Combination of Hydroxychloroquine with Sulphonylureas

| i. Each tablet/capsule contains: | |
|---|---|
| Hydroxychloroquine | 100 mg to 400 mg |
| Glimepiride | 1 mg to 8 mg |

| ii. Each tablet/capsule contains: | |
|---|---|
| Hydroxychloroquine | 100 mg to 400 mg |
| Gliclazide (including Gliclazide modified/controlled release | 30 mg to 320 mg |

| iii. Each tablet/capsule contains: | |
|---|---|
| Hydroxychloroquine | 100 mg to 400 mg |
| Glibenclamide (Glyburide) | 1 mg to 20 mg |

| iv. Each tablet/capsule contains: | |
|---|---|
| Hydroxychloroquine | 100 mg to 400 mg |
| Glipizide | 1 mg to 40 mg |

Example 2

Fixed Dose Combination of Hydroxychloroquine with Biguanides

| i. Each tablet/capsule contains: | |
|---|---|
| Hydroxychloroquine | 100 mg to 400 mg |
| Metformin (including metformin extended/controlled release) | 250 mg to 2500 mg |

Example 3

Fixed Dose Combination of Hydroxychloroquine with Thiazolidinediones

| i. Each tablet/capsule contains: | |
|---|---|
| Hydroxychloroquine | 100 mg to 400 mg |
| Pioglitazone | 10 mg to 45 mg |
| ii. Each tablet/capsule contains: | |
| Hydroxychloroquine | 100 mg to 400 mg |
| Rosiglitazone | 2 mg to 8 mg |

Process for Preparation:

The pharmaceutical composition as described above can be formulated into different dosage forms using suitable conventional pharmaceutical excipients/carrier that can be selected from but not limited to pharmaceutical acceptable polymers, fillers, diluents, glidants, disintegrant, lubricants and the like, using conventional preparative techniques.

The fixed dose formulation of the present invention is preferably in the form of tablets or capsules, wherein tablets/capsules can be prepared in immediate release, modified/controlled release, extended or in sustain release form, where suitable polymeric materials are used to modify the release of drug.

While the present invention is described above in connection with preferred or illustrative embodiments, these embodiments are not intended to be exhaustive or limiting of the invention. Rather, the invention is intended to cover all alternatives, modifications and equivalents included within scope, as defined by appended claims.

I claim:

1. A pharmaceutical composition for use in the treatment and/or management of diabetes comprising hydroxychloroquine or its pharmaceutically acceptable salt, and at least one antidiabetic compound selected from the group consisting of a sulphonylurea, a biguanide, and a thiazolidinedione.

2. A pharmaceutical composition according to claim 1, wherein the sulphonylurea is selected from the group consisting of glimepiride, gliclazide, and glipizide; the biguanide is metformin; and the thiazolidinedione is selected from the group consisting of rosiglitazone and pioglitazone.

3. A pharmaceutical composition according to claim 1, for treatment of diabetes associated with risk of hyperlipidemia or cardiovascular disease.

4. A pharmaceutical composition according to claim 1, for treatment of diabetes associated with risk of platelet aggregation.

5. A pharmaceutical composition according to claim 1, wherein the diabetes is resistant to oral hypoglycaemic agents.

6. A pharmaceutical composition according to claim 1, wherein the hydroxychloroquine ranges from 50 mg to 400 mg.

7. A pharmaceutical composition according to claim 2, wherein the glimepiride ranges from 1 mg to 10 mg.

8. A pharmaceutical composition according to claim 2, wherein the gliclazide ranges from 30 mg to 320 mg.

9. A pharmaceutical composition according to claim 2, wherein the glipizide ranges from 1 mg to 40 mg.

10. A pharmaceutical composition according to claim 2, wherein the metformin ranges from about 200 mg to 2500 mg.

11. A pharmaceutical composition according to claim 2, wherein the pioglitazone ranges from 2 mg to 45 mg.

12. A pharmaceutical composition according to claim 2, wherein the rosiglitazone ranges from 1 mg to 8 mg.

13. A pharmaceutical composition according to claim 1, wherein further comprising pharmaceutical excipients/carriers.

14. A pharmaceutical composition according to claim 13, wherein said formulation is a solid dosage form.

15. A method for treating diabetes comprising the step of administering to a person in need thereof the composition of claim 1.

16. A method for treating diabetes comprising the step of administering to a person in need thereof a pharmaceutical combination of hydroxychloroquine and at least one antidiabetic compound selected from the group consisting of a sulfonyl urea, a biguanide, and a thiazolidinedione.

17. The method of claim 16, wherein the diabetes is resistant to oral hypoglycaemic agents.

18. The method of claim 16, wherein the diabetes is associated with risk of hyperlipidemia or cardiovascular disease.

19. The method of claim 16, wherein the diabetes is associated with risk of platelet aggregation.

* * * * *